United States Patent [19]

Palmer

[11] 4,261,798
[45] Apr. 14, 1981

[54] METHOD OF PURIFYING READILY POLYMERIZABLE VINYL MONOMERS

[75] Inventor: Richard G. Palmer, Carshalton, England

[73] Assignee: BP Chemicals Limited, London, England

[21] Appl. No.: 104,660

[22] Filed: Dec. 17, 1979

[30] Foreign Application Priority Data

Jan. 10, 1979 [GB] United Kingdom ............... 00957/79

[51] Int. Cl.³ .......................................... C07C 69/54
[52] U.S. Cl. ........................................ 203/9; 203/88; 203/94; 203/98; 560/4; 560/218; 562/600
[58] Field of Search .................. 560/218, 4; 562/600; 203/8, 9, 88, DIG. 21, 98, 94

[56] References Cited

U.S. PATENT DOCUMENTS 3,162,677 12/1964 Horsley et al. ................... 560/218
4,053,504 10/1977 Rosenkranz et al. ................... 560/4

Primary Examiner—Frank Sever
Attorney, Agent, or Firm—Brooks, Haidt, Haffner & Delahunty

[57] ABSTRACT

The present invention relates to a method of purifying readily polymerizable high boiling vinyl monomers, in particular the acrylates and methacrylates of alkylene oxides and their ether and ester derivatives to obtain pure water white esters. The process involves flash evaporation of the preheated esters followed by condensation in the presence of polymerization inhibitors under specific conditions. The purified esters thus produced find use either as such or in the form of their copolymers in coatings, enamel paints, weather resistant finishes, adhesive compositions, as plasticizers, as lubricants for cellulose films and fibers, in magnetic tape recording media and as oil additives.

9 Claims, 1 Drawing Figure

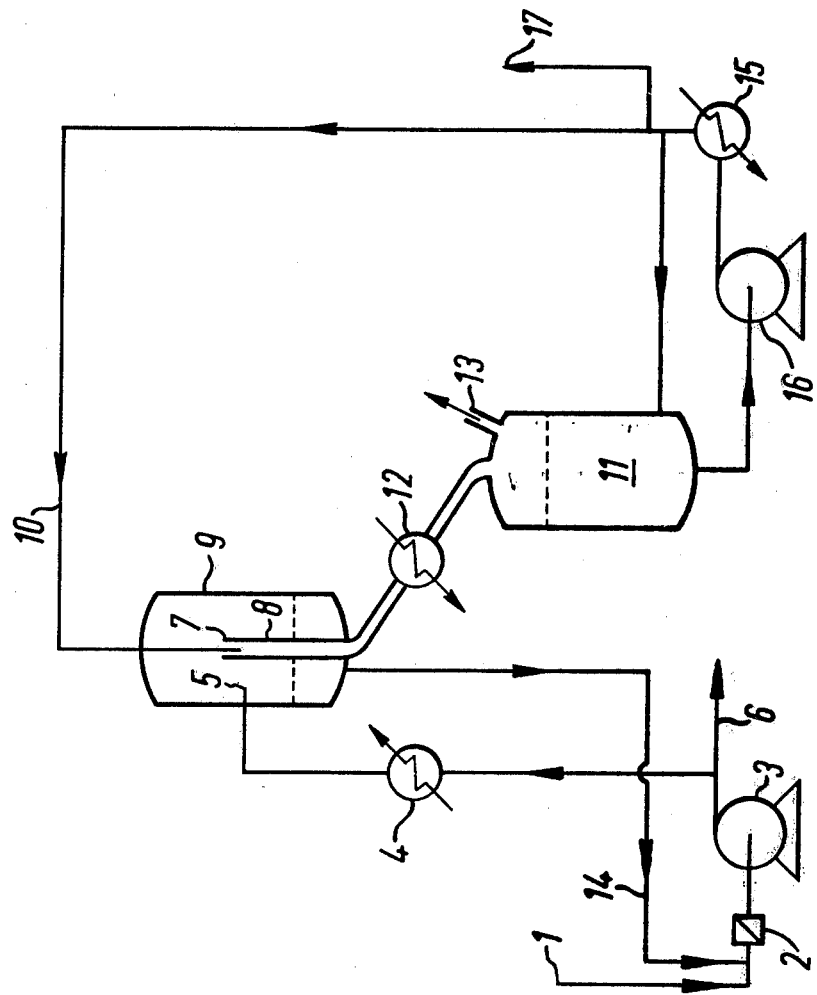

METHOD OF PURIFYING READILY POLYMERIZABLE VINYL MONOMERS

The present invention relates to a method for purifying readily polymerisable vinyl monomers with a view to removing essentially non-volatile and catalyst impurities therefrom.

Almost all of the known vinyl monomers are capable of being polymerised at least to some extent but the degree of polymerisation achieved varies with the type of monomer and the severity of the conditions used for polymerisation. For example some vinyl monomers such as styrene, vinyl acetate, the simple acrylate and methacrylate esters and vinyl halides are relatively stable monomers. These monomers may be purified from their respective impure states as produced by conventional simple distillations or fractional distillation techniques. The purification in the case of these monomers may be achieved without any risk of serious complications due to polymer formation.

Some other vinyl monomers however do not exhibit such stability and are highly polymerisable under the conditions of time, temperature and pressure needed to distil these monomers. The vinyl monomers which are particularly susceptible to ready polymerisation are those monomers which have a boiling point above 170° C. at atmospheric pressure eg hydroxyl alkyl acrylates, hydroxyalkyl methacrylates, glycidyl acrylates and methacrylates, glycol and glycol ether acrylates and methacrylates, and polyol ether acrylates and methacrylates. These vinyl monomers when prepared on a commercial scale inevitably contain essentially non-volatile impurities and organometallic catalyst residues. In the purification of these compounds by conventional distillation or fractional distillation, polymerisation tends to occur and the distillation towers get clogged by the polymers. Attempts to use polymerisation inhibitors such as hydroquinone or phenothiazine in certain cases have also given unsatisfactory results because these inhibitors have very low vapour pressure at the distillation temperatures of the vinyl monomer being purified and hence the monomer vapour which condenses in the upper half of the tower usually contains no inhibitor. This condensed monomer being unstable gives rise to polymer formation nucleating on the interior surface irregularities of the tower. Once such polymerisation is initiated, the rate of polymer formation is uncontrollably accelerated resulting in loss of product and in the shut-down of the distillation unit. If on the other hand, inhibitors with a high vapour pressure such as organic nitroso compounds or hydrazine hydrate are used, they distil over with the monomer and are difficult to separate from the monomer. This can hinder the subsequent use of the monomer and, in its polymerised form, can also cause discolouration.

Hydroxyalkyl acrylates and methacrylates in particular are difficult to distil in that they are highly polymerisable monomers of moderately high boiling point (90°–100°C. at 5–10 mm Hg pressure) which on distillation are likely to polymerise even in the presence of an inhibitor and at reduced temperature and pressure. Furthermore, the unsaturated acids themselves whether used as a reactant or in the catalyst may give rise to resinous products on distillation. In these circumstances, purification to remove the essentially non-volatile impurities and organometallic catalyst residues from the crude ester product is usually carried out by flash evaporation. To obtain a high purity product from a flash evaporation the crude product needs to contain a high percentage of the desired product as there will be relatively little change in composition because of the lack of fractionation. In addition, the evaporation cannot be carried through to recover all the ester in the crude product for fear of polymerisation due to overheating.

A further problem encountered in obtaining pure 2-hydroxyalkyl acrylates and methacrylates in high yields is the presence of excessive quantities of diester materials, such as ethylene glycol diacrylates, which are harmful in that they may lead to the formation of unwanted insoluble cross-linked polymers where the acrylate or methacrylate is used in polymerisation or copolymerisation reactions. Moreover, chromium catalysts used to produce the esters in this particular case gives rise to densely coloured products.

It has now been found that by using a particular separation technique the risk of polymerisation is minimised and a substantially pure product is recovered without any appreciable loss of the product yield.

Accordingly, the present invention is a process for purifying crude, readily polymerisable vinyl monomers which have a boiling point above 170° C. at atmospheric pressure in a separation zone maintained at reduced pressure which comprises pre-heating the crude monomer to a temperature above the boiling point thereof at the prevailing pressure in the separation zone but below the boiling point thereof at atmospheric pressure, introducing the hot crude monomer into the separation zone so that partial vaporisation of the hot crude monomer takes place, the separation zone having means in the upper portion thereof for contacting a liquid stream of cold purified monomer with the vapours of the hot crude monomer so as at least partially to condense them in the cold purified monomer stream thereby separating them from the unvaporised portion of the hot crude monomer, and withdrawing from the separation zone separate liquid streams of cold purified monomer and hot crude monomer.

The separation zone, maintained at reduced pressure, preferably comprises a container, which is suitably a vertically mounted cylinder having a first inlet in the side at about the mid point thereof through which a stream or spray of hot crude monomer can be introduced laterally into the container whereby partial vaporisation of the hot crude monomer takes place. The container also has a second inlet at the top through which a liquid stream or spray of cold purified monomer can be injected downwards into the mouth of an open-ended tube which extends from above the middle of the container down through the base thereof and which serves to withdraw the liquid stream of cold purified monomer from the container. The second inlet and the open ended tube are suitably positioned substantially co-axially within the vertical cylindrical container, and jointly comprise the means for contacting the liquid stream of cold purified monomer with the vapours of the hot crude monomer so as at least partially to condense the vapours in the cold purified monomer stream. The relative positions of the first inlet and the open ended tube are arranged so that only vapours of the hot crude monomer are allowed to contact the cold purified monomer stream passing down the open ended tube. The container also has an outlet located at the base through which the non-vaporised portion of the hot crude monomer can be withdrawn.

In operation the crude monomer is suitably passed through one or more filters to separate any suspended impurities, and is then pre-heated in a heat exchanger under pressure to a temperature above the boiling point of the monomer at the pressure prevailing in the separation zone so that when hot crude monomer is released laterally into the separation zone, the reduced pressure therein ensures partial vaporisation thereof. For example in the case of hydroxypropyl methacrylate the crude monomer is suitably pre-heated to a temperature below 95° C., preferably between 90° C. and 95° C., and the separation zone is maintained at a pressure between 5 and 10 mm Hg and a temperature between 30° and 50° C.

The process may be operated continuously by recycling the non-vaporised crude monomer withdrawn from the base of the separation zone to the crude monomer feed to the pre-heating unit preferably after removal of a purge stream to prevent build-up of residues in the system. Similarly a part of the cold purified monomer stream withdrawn from the separation zone through the open ended tube may be recycled to the second inlet at the top of the container for injection into the mouth of the open ended tube.

The process is suitably operated by using a polymerisation inhibitor in the monomer. The polymerisation inhibitor is preferably selected from p-methoxyphenol, hydroquinone, phenothiazine, pyrogallol, tertiary butyl catechol and mixtures thereof. The concentration of the inhibitor in the crude monomer is suitably between 600 and 700 ppm and that in the purified monomer is suitably between 200 and 250 ppm. Where a phenolic inhibitor such as p-methoxy phenol is used, it is necessary to ensure that there is adequate oxygen available in the monomer for the inhibitor to be effective. This may be achieved by introducing a controlled amount of air-/oxygen into the purification system.

Under these conditions, the product withdrawn from the base of the column is substantially pure monomer.

The readily polymerisable vinyl monomers which have a high boiling point and which may be purified by the present process is preferably selected from hydroxyalkyl acrylates, hydroxyalkyl methacrylates, glycidyl acrylates and methacrylates, glycol and glycol ether acrylates and methacrylates, and polyol ether acrylates and methacrylates.

The present invention is further illustrated with reference to the following Example and the accompanying drawing which is a flow diagram illustrating the purification of an ester according to the present invention

EXAMPLE 1

Preparation of Hydroxypropyl Methacrylate

Methacrylic acid (1720 kg), p-methoxyphenol (1.3 kg) and commercial chromium octanoate (17.2 kg) were charged to a stirred autoclave and agitated to effect solution. The autoclave was evacuated and the vacuum broken to atmospheric pressure with nitrogen. The autoclave and its contents were heated with stirring to 80° C. Propylene oxide (100 kg) was fed to the autoclave and when it had been established that reaction had commenced further propylene oxide (1116 kg) was added over 2½ hours. A maximum pressure of 38 psig was reached. The progress of the reaction was monitored by acid number determinations. When the acid number reached 0.2 the autoclave was cooled to 40° C. and excess propylene oxide was removed under vacuum for 30 minutes. Further vacuum degassing was carried out after transfer to another vessel until the residual propylene oxide content was less than 0.5%. The crude product containing dissolved chromium catalyst was analysed for composition and inhibitor (p-methoxyphenol) content.

Purification of Crude Hydroxy Propyl Methacrylate

After the removal of excess propylene oxide as described above the crude ester product is transferred to a feed tank identified as (1) in the accompanying drawing. From this tank (1) it is fed into filters (2) for removal of suspended solid impurities such as polymers. The filtered material is then pumped by pump (3) to an evaporator (4) in which the temperature is raised to about 90°–95° C. and is then injected through a nozzle (5) into a container (9) laterally through its wall at a point below the top (7) of an open-ended tube (8). The temperature of the container (9) (including the wall thereof) is maintained at about 50° C. and the pressure within the container is maintained at about 5–10 mm Hg by means of a vacuum pump attached to port (13). A spray of cold liquid hydroxypropyl methacrylate, which has already been purified to the desired quality, is introduced in the container (9) via line (10) and is directed down the open-ended tube (8). This cold spray condenses the vapourised portion of the preheated crude ester feed and the condensed vapours are collected from the base of the column in a product tank (11) via a water jacketed cooler (12). The unvapourised portion of the crude ester remaining in the container (9) passes to the bottom thereof and is returned to the fresh feed via line (14).

The purified product in the tank (11) may be transferred to intermediate storage tanks (17) through product coolers (15) using pump (16) and a portion of the purified ester is recycled via line (10) to the container (9).

Throughout the above mentioned process, the only inhibitor used is p-methoxyphenol, to maintain a level of between 600 and 700 ppm in the crude ester and a level of between 200 and 250 ppm in the purified ester. To render the inhibitor effective a controlled air/oxygen bleed is continually fed to the purification system.

In order to prevent the build-up of impurities and residues in a continuous process, a side stream of the residues is continually withdrawn via line (6). The residues may if necessary be redistilled separately. The ester product thus recovered from the base of the tube (8) is substantially pure and water-white in colour.

The purified water-white ester had the following specification:

Colour Hazens Units—10
Acid number (mg KOH/g)—0.15 (0.03% by wt. Acid Content)
Water Content (% by wt.)—0.2
Dipropyleneglycol monomethacrylate (% by wt.)—2
Propyleneglycol dimethacrylate (% by wt.)—0.2
Hydroxypropyl Methacrylate (% by wt.)—97.57

EXAMPLE 2

The process of Example 1 was repeated using an appropriate amount of ethylene oxide instead of propylene oxide. The crude hydroxyethyl methacrylate was purified as in Example 1 and the purified water-white hydroxyethyl methacrylate had the following specification:

Colour Hazens Units—10

Acid number (mg KOH/g)—0.13 (0.026% by wt. Acid Content)

Water Content (% by wt.)—0.1

Diethylene glycol monomethacrylate (% by wt.)—2.0

Ethylene glycol dimethacrylate (% by wt.)—0.3

Hydroxyethyl methacrylate (% by wt.)—97.574

The purified esters thus produced find use either as such or in the form of their copolymers in coatings, enamel paints, weather resistant finishes, adhesive compositions, as plasticizers, as lubricants for cellulose films and fibres, in magnetic tape recording media and as oil additives.

I claim:

1. A process for purifying crude, readily polymerisable vinyl monomers which have a boiling point above 170° C. at atmospheric pressure in a separation zone maintained at reduced pressure which comprises preheating the crude monomer to a temperature above the boiling point thereof at the prevailing pressure in the separation zone but below the boiling point thereof at atmospheric pressure, introducing the hot crude monomer into the separation zone so that partial vaporisation of the hot crude monomer takes place, providing in the separation zone a means in the upper portion thereof for contacting a liquid stream of cold purified monomer with the vapours of the hot crude monomer so as at least partially to condense them in the cold purified monomer stream thereby separating them from the unvaporised portion of the hot crude monomer so as to minimize polymerisation of the monomer, and withdrawing from the separation zone separate liquid streams of cold purified monomer and hot crude monomer.

2. A process according to claim 1 wherein the separation zone comprises providing a container which is a vertically mounted cylinder having a first inlet in the side at about the mid point thereof for introducing the hot crude monomer, a second inlet at the top thereof for introducing the cold purified monomer and an open-ended tube which extends from above the middle of the container down through the base thereof, the second inlet and the open-ended tube being positioned substantially co-axially within the container, and an outlet located at the base thereof for withdrawing the non-vapourised portion of the hot crude monomer.

3. A process according to claim 2 wherein the process is operated continuously by recycling (i) the non-vapourised hot crude monomer withdrawn from the base of the container to the crude monomer feed to the preheating unit and (ii) a part of the cold purified monomer stream withdrawn from the separation zone to the second inlet at the top of the container.

4. A process according to claim 1 wherein the readily polymerisable vinyl monomer is selected from hydroxyalkylacrylates, hydroxyalkylmethacrylates, glycidyl acrylates, glycidyl methacrylates, glycol acrylates, glycol methacrylates, glycol ether acrylates, glycol ether methacrylates, polyol ether acrylates and polyol ether methacrylates.

5. A process according to claim 4 wherein the hydroxy alkylmethacrylate is hydroxypropylmethacrylate.

6. A process according to claim 4 wherein said process is carried out in the presence of a polymerisation inhibitor.

7. A process according to claim 6 wherein the polymerisation inhibitor is selected from p-methoxyphenol, hydroquinone, phenothiazine, pyrogallol, tertiarybutyl catechol and mixtures thereof.

8. A process according to claim 5 wherein the crude hydroxypropylmethacrylate is preheated to a temperature between 90° and 95° C.

9. A process according to claim 5 wherein the separation zone is maintained at a pressure between 5 and 10 mm Hg and a temperature between 30° and 50° C.

* * * * *